United States Patent [19]

Taylor et al.

[11] Patent Number: 5,136,058
[45] Date of Patent: Aug. 4, 1992

[54] PROCESS FOR THE RECOVERY OF PURIFIED GAMMA-BUTYROLACTONE IN HIGH YIELD FROM ITS CRUDE REACTOR EFFLUENT

[75] Inventors: Paul D. Taylor, West Milford, N.J.; Michael Aversa, League City, Tex.; Waldo De Thomas, Saylorsburg, Pa.; Donald Buchanan, Wayne, N.J.

[73] Assignee: ISP Investments Inc., Wilmington, Del.

[21] Appl. No.: 735,556

[22] Filed: Jul. 25, 1991

[51] Int. Cl.$^5$ .......................................... C07D 307/28
[52] U.S. Cl. ......................................................... 549/326
[58] Field of Search ............................................ 549/326

[56] References Cited

U.S. PATENT DOCUMENTS

| | | | |
|---|---|---|---|
| 3,065,243 | 11/1962 | Dunlop et al. | 549/326 |
| 4,069,232 | 1/1978 | Horvitz et al. | 549/326 |
| 4,945,173 | 7/1990 | Wood | 549/326 |

FOREIGN PATENT DOCUMENTS 8607358 12/1986 PCT Int'l Appl.
8800937 2/1988 PCT Int'l Appl.

Primary Examiner—C. Warren Ivy
Assistant Examiner—Amelia A. Owens
Attorney, Agent, or Firm—Walter Katz; Marilyn J. Maue; Joshua J. Ward

[57] ABSTRACT

This invention relates to a process for the recovery of purified gamma-butyrolactone (BLO) in high yield from its crude reactor effluent containing BLO, tetrahydrofuran (THF), water, the acid-catalyzed hydrolysis product of BLO which is 4-hydroxybutyric acid (4-HBA), light and heavy organic acids, and alcohols. The process is particularly characterized by flash vaporizing a THF-free mixture of BLO, 4-HBA, water, light acids such as butyric acid and propionic acid, and alcohols so that the 4-HBA component is recyclized to form additional BLO. Heavy acids such as succinic acid and maleic acid are removed from the bottom.

The total amount of BLO in the vapor stream then is fed to a distillation column where it is condensed; the water, including the water of dehydration, and light acid and alcohol impurities in the distillation are separated overhead from the BLO and removed. This procedure prevents BLO from further acid hydrolysis while the water of dehydration from 4-HBA is recovered.

8 Claims, 1 Drawing Sheet

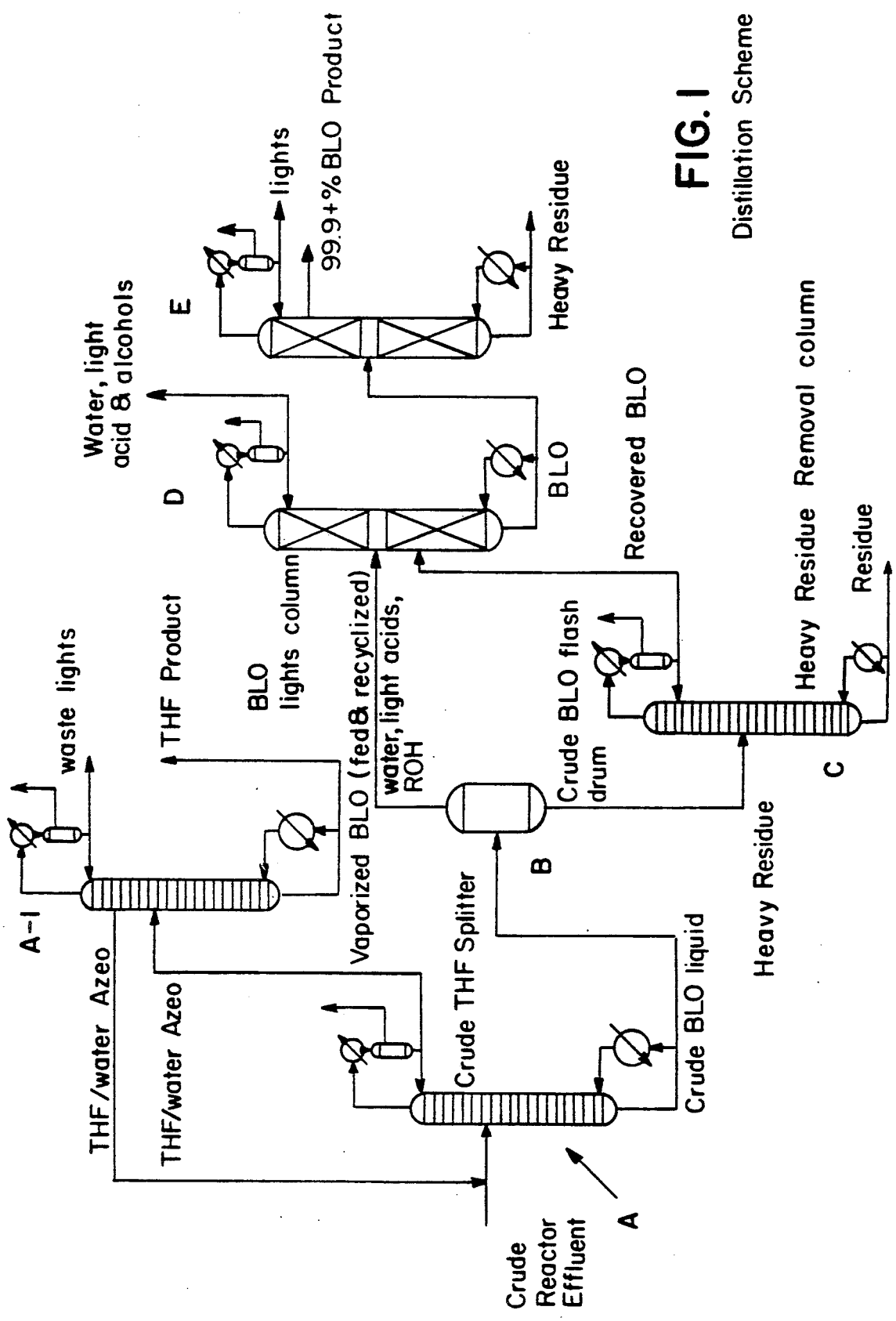
FIG. 1 Distillation Scheme

PROCESS FOR THE RECOVERY OF PURIFIED GAMMA-BUTYROLACTONE IN HIGH YIELD FROM ITS CRUDE REACTOR EFFLUENT

BACKGROUND OF THE INVENTION

1. Field of the Invention

This invention relates to the production of gamma-butyrolactone, and, more particularly, to a process for the recovery of purified BLO in high yield from its crude reactor effluent.

2. Description of the Prior Art

Attig, in EPO 322,140, published Jun. 28, 1989, described a process for the production of THF and BLO in which the reaction products of THF and BLO were separated by fractional distillation; by-products and unreacted feed, were returned to the hydrogenation stage; and acidic by-products were removed by treatment with alkali before distillation.

Franko-Filipasic, in U.S. Pat. No. 3,113,138, described a liquid phase process for making BLO by catalytic hydrogenation of succinic anhydride in an organic solvent; recovering the BLO by filtering to remove catalyst; distilling at atmospheric pressure to remove solvent and water; and distilling the product residue at reduced pressure.

Wada, in U.K. patent application No. 2,194,232, published Mar. 2, 1988, while describing a method for making BLO, stated that "the desired lactone may be recovered from the reaction solution by a usual separation and purification means such as distillation or extraction. Further, the distillation residue may be recycled to the reaction system as a catalyst component".

Dunlop, in U.S. Pat. No. 3,065,243, was directed to the reduction of dicarboxylic acid esters and anhydrides to BLO by catalytic hydrogenation in the vapor phase; the process gave a mixed condensate comprising succinic anhydride, BLO and water, which was fractionally distilled to provide BLO in 70-80% conversion.

Broecker, in U.S. Pat. No. 4,048,196, described a multi-stage process for the manufacture of butanediol and/or THF from maleic and/or succinic anhydride via BLO. In the first stage, maleic anhydride, or succinic anhydride, was hydrogenated in the presence of added BLO over a fixed-bed catalyst to give BLO; then the water formed during the hydrogenation was removed by feeding the reaction mixture to the middle section of a distillation column; followed by isolating water and BLO, on one hand, and succinic anhydride and BLO, on the other hand; recycling succinic anhydride and BLO; and finally, separating BLO and water by distillation.

Kouba, in U.S. Pat. No. 4,656,297, described a process for the coproduction of butanediol and THF and their subsequent separation from the reaction product mixture containing water and methanol by a series of distillations including a superatmospheric distillation.

Other references, including DeThomas, U.S. Pat. No. 4,105,674; Mitsubishi, Japan 49-9463; Michalczyk, U.S. Pat. No. 4,006,165; Miya, U.S. Pat. No. 3,580,930; Miller, U.S. Pat. No. 4,001,282; Michalczyk, U.S. Pat. No. 3,948,805; Bridge, U.S. Pat. No. 4,810,807; and Tonen, EPO 373,946; described related processes, without, however, mentioning the separation and/or purification of the desired product from its reaction effluent mixture.

Vapor phase catalytic hydrogenation of maleic anhydride to BLO under high conversion and high selectivity conditions can be carried out by passing a vapor mixture of maleic anhydride feed compound and hydrogen over a suitable catalyst of defined composition. What is desired, however, is to recover the BLO product in purified form and in high yield from the crude reactor effluent which includes in addition to BLO, tetrahydrofuran (THF), water, organic acids and alcohols; and, as has been discovered herein, a small amount of 4-hydroxybutyric acid, which is formed by acid-catalyzed hydrolysis of BLO.

Accordingly, it is an object of this invention to provide a process for the recovery of purified BLO in high yield from its crude reactor effluent.

Another object of the invention is to upgrade the yield of purified BLO from the crude reaction effluent by dehydration and cyclization of the 4-HBA component present in the crude reactor effluent to BLO while separating and removing the water of dehydration to prevent renewed acid hydrolysis of the BLO.

These and other objects and features of the invention will be made apparent from the following description thereof.

DESCRIPTION OF THE DRAWING

The FIGURE is a flow chart illustrating the several steps in the process of the invention.

SUMMARY OF THE INVENTION

This invention relates to a process for the recovery of purified gamma-butyrolactone (BLO) in high yield from its crude reactor effluent containing BLO, tetrahydrofuran (THF), water, the acid-catalyzed hydrolysis product of BLO which is 4-hydroxybutyric acid (4-HBA), light and heavy organic acids, and alcohols. The process is particularly characterized by flash vaporizing a THF-free mixture of BLO, 4-HBA, water, light acids such as butyric acid and propionic acid, and alcohols so that the 4-HBA component is recyclized to form additional BLO. Heavy acids such as succinic acid and maleic acid are removed from the bottom.

The total amount of BLO in the vapor stream then is fed to a distillation column where it is condensed; the water, including the water of dehydration, and light acid and alcohol impurities in the distillation are separated overhead from the BLO and removed. This procedure prevents BLO from further acid hydrolysis while the water of dehydration from 4-HBA is recovered.

DETAILED DESCRIPTION OF THE INVENTION

The vapor phase catalytic hydrogenation of maleic anhydride provides a crude reactor product having the following composition:

| COMPOSITION OF CRUDE REACTOR PRODUCT | |
|---|---|
| | Wt. % |
| Butyrolactone* | 70–75 |
| 4-Hydroxybutyric Acid | 1–20 |
| Water | 15–25 |
| Tetrahydrofuran | 1–5 |
| Alcohols | 1–5 |
| Butanediol | 0.1–4 |
| Light Acids | 0.1–1 |
| Succinic Acid | 0.1–1 |

*formed by the acid-catalyzed hydrolysis of BLO during the hydrogenation process.

Referring now to the FIGURE, the process begins with the introduction of the crude reactor effluent into the crude splitter Column A which is operated at a pressure of about 1 atmosphere. The purpose of the Crude Splitter Column is to separate THF from the rest of the crude reactor product. The THF is removed as a THF-water azeotrope overhead from a packed tower; the rest of the crude product, which contains, in addition to BLO, some 4-HBA, water, acids and alcohols, and other lights and heavies, are removed at the bottom of the column.

The overhead 95-5% THF-water azeotrope then is fed into the THF Azeotrope Column A-1. A THF-water azeotrope then is withdrawn as a side-draw from the column, and it is recycled to the Crude Splitter Column A. Anhydrous THF is withdrawn from the bottom of the Column A-1 where it can be further purified, if desired. The lighter components present in Column A-1 are removed overhead.

The bottoms from the Crude Splitter Column A then are fed to the Crude BLO Vaporizer Unit B which operates at a reduced pressure of 50-500 mm Hg and a temperature of 125°-200° C. Unit B performs two functions; first, it dehydrates and recyclizes the 4-HBA component of the mixture to BLO by means of its controlled temperature, reduced pressure and holding time. Second, it will vaporize the entire mixture, including an additional amount of BLO thus formed, except for the heavy residues, e.g. heavy acids such as succinic acid, which are removed as liquids from the bottom of the unit. Preferably the holding time for the mixture in Unit B is about 1-10 hours (on net feed). The proportion of the vaporized feed usually is about 65 to 96 wt. % of the feed mixture. The vapor feed contains vaporized BLO, water, organic acids and organic alcohols. The residues are sent to the Heavy Residue Removal Column C where some BLO is recycled into the system.

Then a vapor feed from overhead Unit B and recovered crude BLO from the overhead of Column C are continuously fed into the BLO Lights Column D which operates at 50-500 mm Hg pressure and at a temperature of about 125°-200° C. In BLO Lights Column D, water and light boiling impurities remain as a vapor and are removed overhead while BLO is condensed to a liquid and separated by bottom removal, substantially free of 4-HBA. The BLO liquid contains about 95-99 wt. % BLO; it is then fed into the BLO Product Column E which operates at about 50-300 mm Hg and about 125°-175° C. The BLO Product Column has three functions; first, it will permit withdrawal of high purity liquid BLO (99.+mol %) by distillation from the side or overhead of the column; second, it will separate a small quantity of light boiling impurities via the overhead from the BLO product; and third, it will enable the removal of heavy residues from the bottom of the column. Substantially no water is present in this column, thus assuring that the BLO product will contain less than 0.05% water therein.

The invention thus provides the desired BLO product, in an upgraded amount, due to the conversion of 4-HBA into additional BLO, and in highly purified form, substantially free of the other impurities in the crude hydrogenation reactor effluent, in high yield, and in a, commercially acceptable process.

While the invention has been described with particular reference to certain embodiments thereof, it will be understood that changes and modifications may be made which are within the skill of the art. Accordingly, it is intended to be bound only by the following claims, in which:

What is claimed is:

1. In a process for the recovery of purified gamma-butyrolactone product in upgraded yield from the crude reactor effluent of the catalytic hydrogenation of maleic anhydride which contains butyrolactone and 4-hydroxybutyric acid, the step of dehydrating and cyclizing the 4-hydroxybutyric acid to additional gamma-butyrolactone, thereby to upgrade the yield of recovered, purified butyrolactone product.

2. A process according to claim 1 wherein the step of dehydration and cyclization of 4-hydroxybutyric acid in the process is carried out at elevated temperatures and reduced pressures to form a crude vapor feed containing butyrolactone and water, hereas heavy acids are bottom removed as a liquid.

3. A process according to claim 2 wherein the butyrolactone in the vapor feed then is condensed to a liquid and bottom removed substantially free of 4-hydroxy butyric acid, while the water and any light acids present are removed overhead.

4. A process according to claim 2 wherein said temperature is about 125°-200° C. and said reduced pressure is about 50-500 mm Hg.

5. A process according to claim 1 wherein the step of dehydration and cyclization is carried out for a period of about 1 to 10 hours.

6. A process according to claim 1 which includes the additional step of first separating and removing tetrahydrofuran from the crude reactor effluent by azeotropic distillation.

7. A process according to claim 2 wherein the crude vapor feed also includes water present originally in the effluent, and light organic acids and alcohols.

8. A process according to claim 3 wherein liquid butyrolactone is further purified by distillation in the substantial absence of water and acids.

* * * * *